United States Patent
Lassila et al.

(10) Patent No.: US 12,268,762 B2
(45) Date of Patent: Apr. 8, 2025

(54) DENTAL COMPOSITION

(71) Applicant: Stick Tech Oy, Turku (FI)

(72) Inventors: Lippo Lassila, Lielax (FI); Pekka Vallittu, Kuusisto (FI); Sufyan Garoushi, Turku (FI); Eija Säilynoja, Littoinen (FI); Jingwei He, Guangzhou (CN)

(73) Assignee: Stick Tech Oy, Turku (FI)

( * ) Notice: Subject to any disclaimer, the term of this patent is extended or adjusted under 35 U.S.C. 154(b) by 1093 days.

(21) Appl. No.: 17/268,184

(22) PCT Filed: Aug. 1, 2019

(86) PCT No.: PCT/EP2019/070738
§ 371 (c)(1),
(2) Date: Feb. 12, 2021

(87) PCT Pub. No.: WO2020/035321
PCT Pub. Date: Feb. 20, 2020

(65) Prior Publication Data
US 2021/0315780 A1    Oct. 14, 2021

(30) Foreign Application Priority Data
Aug. 13, 2018 (EP) ................................ 18188611

(51) Int. Cl.
| | | |
|---|---|---|
| *A61K 6/887* | (2020.01) | |
| *A61K 6/30* | (2020.01) | |
| *A61K 6/35* | (2020.01) | |
| *A61K 6/71* | (2020.01) | |
| *A61K 6/75* | (2020.01) | |
| *A61K 6/76* | (2020.01) | |
| *A61K 6/77* | (2020.01) | |
| *A61K 6/889* | (2020.01) | |

(52) U.S. Cl.
CPC ............... *A61K 6/887* (2020.01); *A61K 6/30* (2020.01); *A61K 6/35* (2020.01); *A61K 6/71* (2020.01); *A61K 6/75* (2020.01); *A61K 6/76* (2020.01); *A61K 6/77* (2020.01); *A61K 6/889* (2020.01)

(58) Field of Classification Search
None
See application file for complete search history.

(56) References Cited

U.S. PATENT DOCUMENTS 5,084,538 A      1/1992  Suzuki et al.
2009/0258965 A1* 10/2009 Lassila ............. A61K 6/54
                                            523/116

FOREIGN PATENT DOCUMENTS

| JP | 3179015 B2 | 6/2001 |
|---|---|---|
| JP | 2004300066 A | 10/2004 |
| JP | 2013144579 A | 7/2013 |
| RU | 2573997 C2 | 1/2016 |
| WO | WO2013028397 A2 | 2/2013 |

OTHER PUBLICATIONS

He et al (Dental Materials, 31(5), 2015, 575-582) (Year: 2015).*
He et al: Preparation of antibacterial and radio-opaque dental resin with new polymerizable quaternary ammonium monomer—Science Direct. Dental Material, May 1, 2015, vol. 31, pp. 575-582.

* cited by examiner

Primary Examiner — Celeste A Roney
(74) Attorney, Agent, or Firm — Timothy H. Van Dyke; Wolter, Van Dyke, Davis PLLC

(57) ABSTRACT

A dental composition comprising 10-50 wt-% of a methacrylate-based first matrix component, a polymerisation system and as a second matrix component 1-50 wt-% of a compound having a general formula (I).

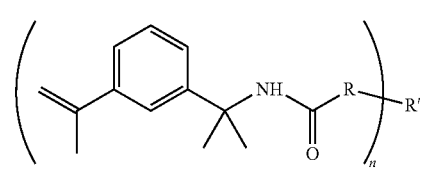

FIG. 1

11 Claims, 2 Drawing Sheets

DENTAL COMPOSITION

FIELD OF THE INVENTION

The present invention relates to a dental composition comprising 10-50 wt-% of a methacrylate-based first matrix component and a polymerisation system.

BACKGROUND AND OBJECTS OF THE INVENTION

Dental compositions are used as filling material of teeth (i.e. as restorative materials), dental cements, liner or dental adhesives. They may comprise filler material and/or reinforcing fibres. depending on the intended use. Typical dental compositions comprise at least one matrix monomer, which is polymerised in situ, i.e. in place in the patient's tooth. Polymerisation, also called curing, may be induced by a chemical initiator, by light, by ultrasound etc. Many dental compositions are based on various methacrylates, which are well known and tolerated.

The dental compositions are typically surrounded by natural tooth, i.e. by dentin and enamel. It would be preferable if the mechanical properties of the restorative material were either similar or better than those of enamel and dentin.

One known problem with the current dental compositions is the shrinking that occurs when the composition is cured, i.e. polymerised. The shrinking may not be visible to the eye and can be typically 2-5 vol %. Shrinkage causes stress at interface of filling material and tooth. The shrinkage stress creates problems in that the dental material, such as dental filling material. When polymerization shrinking occurs, filling material can be (partly) detached from tooth. Thus, the bonding deteriorates, marginal leakage is formed and filling material may thus become loose, cause hypersensitivity and collect bacterial between the material and the tooth, which will lead to further problems.

An aim of the present invention is thus to provide a dental composition that at least partially overcomes the problems of prior art. Indeed, it is an object to provide a dental material that has a low shrinkage stress when cured, while maintaining at the same time good mechanical properties.

DETAILED DESCRIPTION

Figure 1:
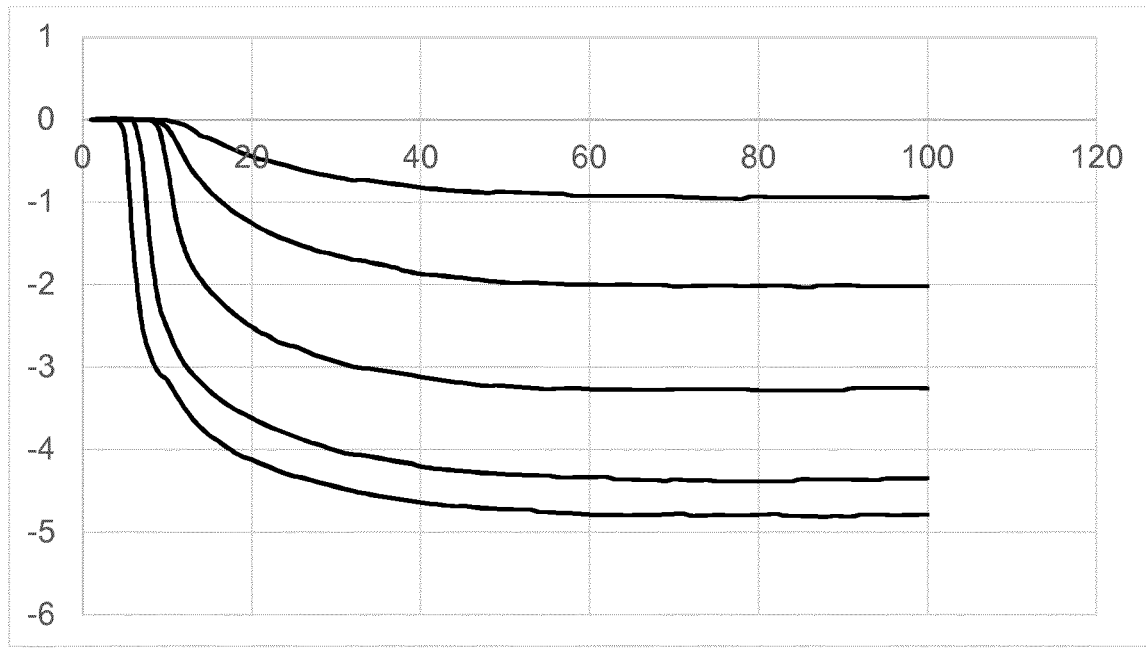
FIG. 1 illustrates the shrinkage stress curves of samples prepared according to Example 4.

The present invention relates to a dental composition comprising 10-50 wt-% of a methacrylate-based first matrix component, a polymerisation system and as a second matrix component 1-50 wt-% of a compound having a general formula (I)

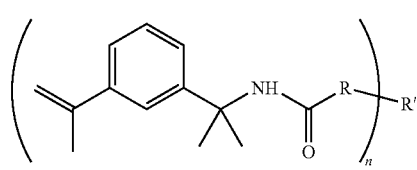

(I)

wherein when n=1, R=NH, R' is (Ia) or (Ib)

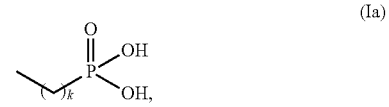

(Ia)

wherein k is 2 or 3,

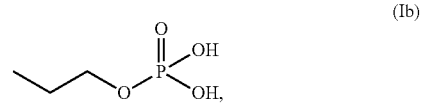

(Ib)

and
when n=2, R=O, R' is (Ic) or (Id),

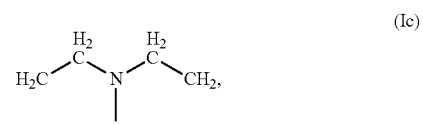

(Ic)

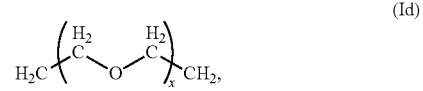

(Id)

wherein x=1-12,
when n=2, R=NH or O, R' is (Ie),

(Ie)

wherein m=0-16, and
when n=2, R=O, R' is (If)

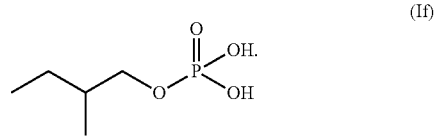

(If)

The present dental composition thus comprises a second matrix component, which has the general formula (I). This second matrix component has been found to decrease the polymerisation shrinkage stress without having a negative effect on the mechanical properties of the composition, as is demonstrated below in the Experimental part. Therefore, the present composition at least partly solves the problem of polymerisation shrinkage stress of dental compositions.

The matrix materials are preferably in their uncured form in the dental composition before its application and are cured once the composition is placed into its final position (such as in a dental cavity to be restored).

The curing may be induced by light, heat or by a combination of an initiator/activator and light, or other wave energy such as UV or ultrasonic activation. By curing, it is meant either polymerisation or cross-linking or similar. The percentages in this description are weight-percentages (wt-%) of the total amount of components (in un-cured form), unless otherwise stated. Since the matrix materials are in uncured form, the composition may also be called a prepreg. That is, a prepreg is an uncured composite, i.e. it contains all the components of the finished composite material, but the matrix material is still in monomer form, or when a cross-linkable matrix material is used, it its non-crosslinked form.

In the present description, the terms "matrix component", "matrix" and "monomer" are used interchangeably and have the same meaning. i.e. the first or second matrix component of the dental composition, and of the finished (cured) product. By "matrix component" it is meant a component that is uniformly distributed within the composition.

The second matrix material is selected from the following compounds.

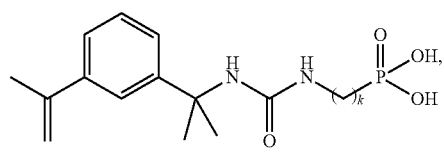
(Ia)

wherein k is 2 or 3, wherein m=0-16

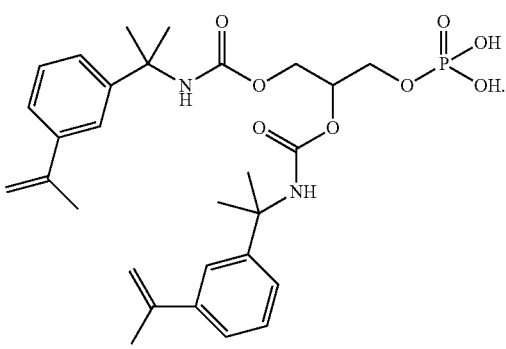
(If)

Some examples of synthesis routes for these compounds are given below.

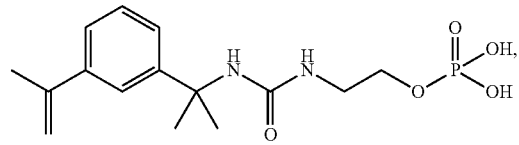
(Ib)

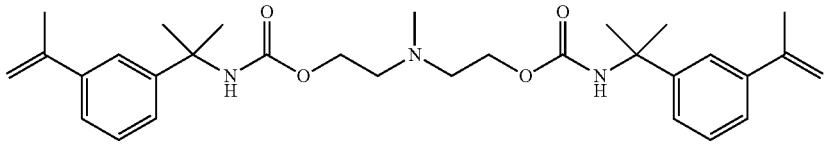
(Ic)

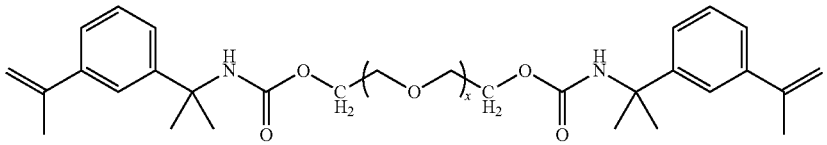
(Id)

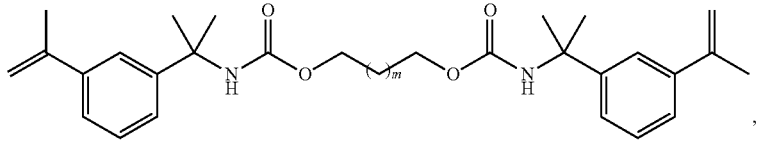
(Ie₁)

wherein m=0-16

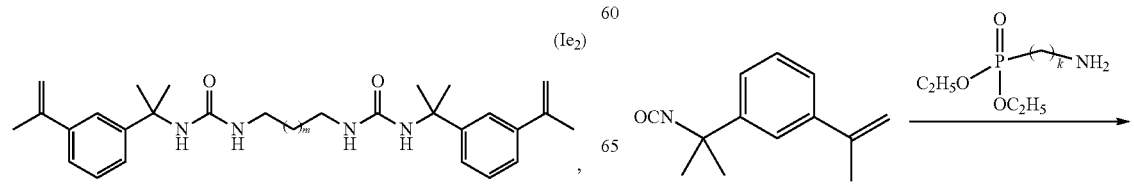
(Ie₂)

Synthesis for Compound (Ia):

-continued
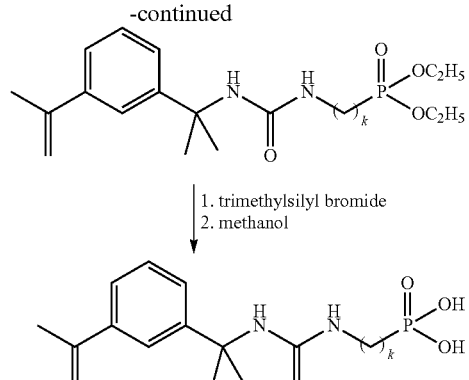
1. trimethylsilyl bromide
2. methanol
Synthesis for Compound (Ib):
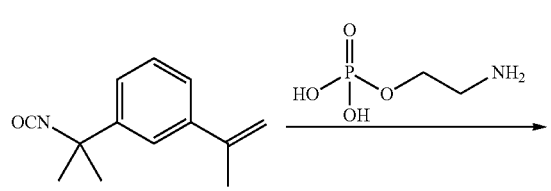
Synthesis for Compound (Ic):
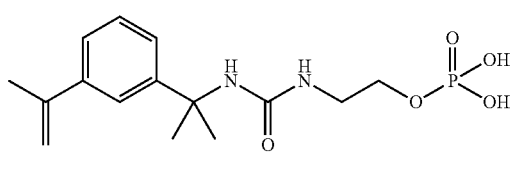
Synthesis for Compound (Id):
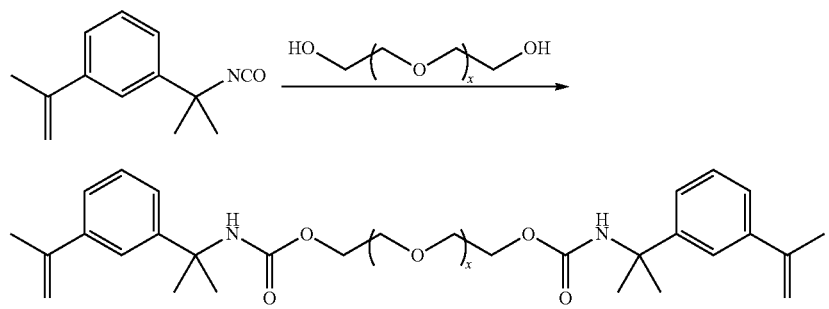
Synthesis for Compounds (Ie):
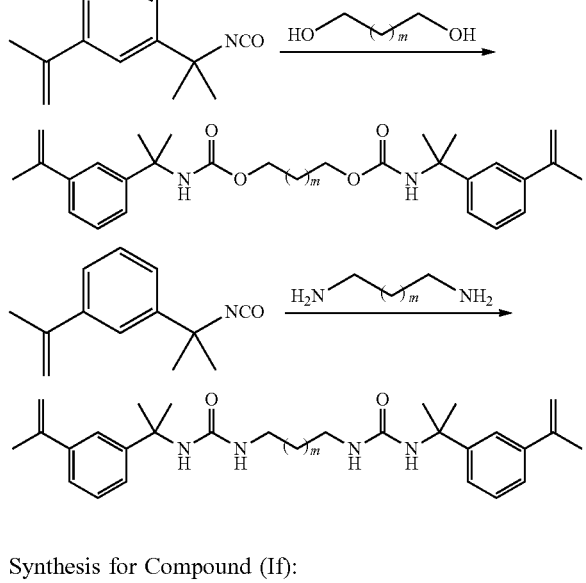
Synthesis for Compound (If):
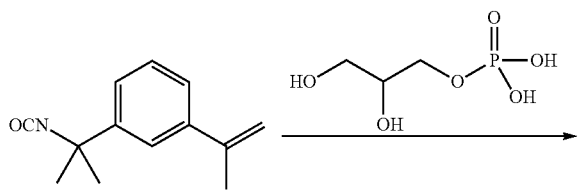

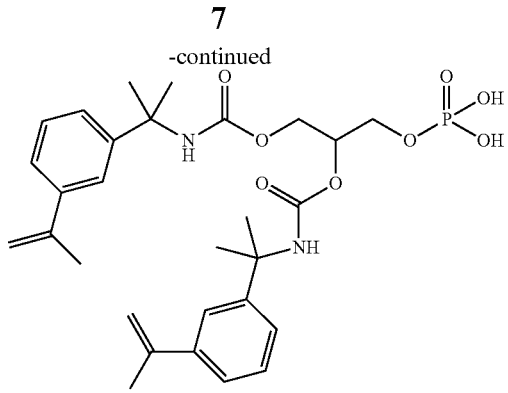

The amount of the first matrix component may be for example 30-50 wt-%. Indeed. the amount of the first matrix component may be from 10, 15, 20, 25, 30, 35, 40 or 45 wt-% up to 15, 20, 25, 30, 35, 40, 45 or 50 wt-%.

The amount of the second matrix component may be 3-35 wt-%. Indeed, the amount of the second matrix component may be from 1, 2, 3, 5, 7, 10, 15, 20, 25, 30, 35, 40 or 45 wt-% up to 2, 3, 5, 7, 10, 15, 20, 25, 30, 35, 40, 45 or 50 wt-%.

The dental composition may further comprise 10 to 45 wt-% of a methacrylate-based third matrix component different from the first matrix component. In other words, the composition may comprise two or more different methacrylate-based matrix components.

Typically. the amount of the second matrix component is equal to or smaller than the amount of the first matrix component. When three matrix components are used, the amount of the second matrix component is typically equal to or smaller than the total amount of the first and third matrix component.

The methacrylate-based matrix component(s) of the dental composition may be any such monomer or polymer suitable for medical use. For example, the methacrylate-based component may be made of monomers selected from the group consisting of methyl methacrylate, ethyl methacrylate, n-butyl methacrylate, isobutyl methacrylate, 2-ethylhexyl methacrylate, cyclohexyl methacrylate, isobornyl methacrylate, tetrahydrofurfuryl methacrylate, benzyl methacrylate, morpholinoethyl methacrylate, acrylic acid, diethylene glycol dimethacrylate, triethylene glycol dimethacrylate (TEGDMA), diurethane dimethacrylate, 10-methacryloyloxydecyl dihydrogen phosphate, 2,2-bis(4-(2-hydroxy-3-methacryloxy)phenyl)propane (BisGMA), methacrylate functionalized dendrimers, other methacrylated hyperbranched oligomers.

One advantageous first matrix component is triethyleneglycol dimethacrylate (TEGDMA) and an advantageous third matrix component is 2,2-bis(4-(2-hydroxy-3-methacryloxy)phenyl)propane (BisGMA).

The matrix material may further comprise crosslinkable monomers or polymers such as crosslinkable polymers derived from ε-caprolactone, polycaprolactone, polylactides, polyhydroxyproline, and other biopolymers as well as polyamides, polyurethane, polyethylene, polypropylene and other polyolefins. The matrix material may naturally also consist of a mixture of a monomer(s) and a polymer(s).

The amount of the matrix materials in the dental composition can be 40-99.5 wt-% of the total weight of the composite material. According to one embodiment the amount of the matrix materials in the composition can be 50-90 wt-% of the total weight of the composition. The amount of matrix materials can be for example from 40, 45, 50, 55, 60, 65, 70, 75, 80, 85 or 90 wt-% up to 45, 50, 55, 60, 65, 70, 75, 80, 85, 90, 95 or 99.5 wt-% of the composition. The uncured matrix material can be for example a monomer mixture comprising a solvent or a mixture of monomers without solvent. When the matrix material in its uncured form comprises a solvent (e.g. ethanol, acetone, water) the solvent is typically removed from the composite material before curing e.g. using air blow or evaporation.

The polymerisation system may be any known initiator and/or activator suitable for medical use. For example, it may be the initiator camphorquinone (CQ) and the activator 2-(dimethylamino) ethyl methacrylate (DMAEMA). It is typically used in an amount of 0.5-2 wt-% of the total weight of the composition.

The dental composition may further comprise a filler material. The filler material, typically in the form of particulate filler material, is typically selected such that it gives to the finished composite material its desired wear resistance, colour and radio-opacity. It typically also influences the shrinkage of the composite material compared to a composite material without any fillers and increases its resistance to wear. The filler material is preferably inorganic filler material.

The filler material may be selected from a group consisting of glass ionomer fillers. colour pigments. inert ceramics. hydroxyl apatite, $Al_2O_3$, $ZrO_2$, silver (Ag), zerogels, YbF3, calcium phosphate, calcium carbonate, bioactive glasses, radio-opaque materials, precured polymer particles and mixtures thereof.

According to another embodiment the particular filler material is selected from the group consisting of inert or bioactive or partially reactive glass ionomer fillers containing elements such as silicon (Si), calcium (Ca), phosphorus (P), barium (Ba), magnesium (Mg), potassium (K), sodium (Na), titanium (Ti), bismuth (Bi), strontium (Sr) or zinc (Zn) oxides or other compounds of said elements, or fluorine (F). The composition may also further comprise filler particles containing functional bioactive or therapeutically active molecules, antigens, antibiotics, growth factors, bone morphogenic proteins (BMPs), interferons, dopamine, corticosteroids, bisphosphonates, cytostatics, anabolic hormones, vitamins, anti-inflammatory agents, antimicrobiotics, disinfectants, organic acids such as maleic acids, polyacrylic acid, or the like, and combinations and mixtures thereof.

By particles, it is meant also for example spheres and very short fibres (where the length of the fibre is at most two times its diameter), like whiskers i.e. having a length below <50 µm. The diameter of the particles in the filler material (this being the largest diameter in case of irregular particles) may vary for example from 10 nm to 50 µm. The diameter can be for example from 10 nm, 50 nm, 100 nm, 500 nm, 1 µm, 5 µm, 10 µm, 25 µm or 40 µm up to 50 nm, 100 nm, 500 nm, 1 µm, 5 µm, 10 µm, 25 µm, 40 µm or 50 µm. Some preferred ranges are 100 nm-40 µm.

The particular filler material may also comprise either partly or fully glass ionomer powder. One type of glass ionomer powders is acid-soluble calcium fluoroaluminosilicate glass particles, which react with a reactive solvent and form a glass ionomer. The reactive solvent is typically poly(acrylic acid) (concentration between 40 to 50%) or a co-polymer or acrylic acid with itaconic, maleic, or tricarboxylic acids. The glass ionomer powder may have particles in the range of 5 to 50 µm. Typical percentages of the raw materials for glass ionomer powder are:

silica 41.9 wt-%
alumina 28.6 wt-%
aluminium fluoride 1.6 wt-% calcium fluoride 15.7 wt-%
sodium fluoride 9.3 wt-%
aluminium phosphate 3.8 wt-%.

The dental composition may still further comprise a fibre reinforcing material. Indeed, fibre-reinforcing typically leads to composite materials having good mechanical properties. According to an embodiment, the fibre reinforcing material is selected from a group consisting of inert glass fibres, bioactive glass fibres, sol-gel processed silica fibres, aluminium oxide-based fibres, zirconia fibres, apatite fibres, quartz fibres and mixtures thereof or polymer-based fibres made of aramid, polyethylene, polypropylene, micro/nano fibrillated cellulose, chitin or polyphenols. Preferably, the fibres are inert glass fibres.

The diameter of the fibres used may vary from 4 µm up to 12 µm. The diameter can thus be for example from 4, 4.5, 5, 5.5, 6, 6.5, 7, 7.5, 8, 8.5, 9, 9.5, 10, 10.5, 11 or 11.5 µm up to 4.5, 5, 5.5, 6, 6.5, 7, 7.5, 8, 8.5, 9, 9.5, 10, 10.5, 11, 11.5 or 12 µm.

The average length of the fibres can be from 50 µm to 1300 µm. such as from 50, 75, 100, 200, 300, 400, 500, 520, 550, 600, 650, 700, 800, 900, 1000, 1050 or 1200 µm up to 75, 100, 200, 300, 400, 550, 600, 750, 800, 900, 1000, 1100, 1200 or 1300 µm depending on fibre diameter.

The total amount of particular filler material and fibres may be 10-60 wt-% of the total weight of the composition. According to one embodiment the amount of particular filler material may be 5-50 wt-% and the amount of fibres can be 5-50 wt-%. The total amount of particular filler material and fibres of the composition can be for example from 10, 15, 20, 25, 30, 35, 40, 45, 50 or 55 wt-% up to 15, 20, 25, 30, 35, 40, 45, 50, 55 or 60 wt-% of the composite.

The present dental composition, especially when used as a dental adhesive, may also comprise a solvent. Such solvent naturally needs to be suitable for medical application and easily volatile.

The present description also relates to use of the present composition as a dental restoration material, a dental adhesive, a dental cement, a post and core material, an endocrown material or for a pontic in fixed partial dentures. The present description further relates to use of the composition in medical applications. The various embodiments and variations listed above apply mutatis mutandis to the use of a composition, be it in dental or in medical applications in general.

The compounds of formula (I) containing phosphate (i.e. compounds of formulas (Ia), (Ib) and (If)) are especially suitable for use in adhesives. In the case they are used in dental adhesives, fillers are typically not used.

For use as a dental filling material or in a composite, the non-phosphate containing compounds of formula (I) are preferred, i.e. the compounds of formulas (Ic), (Id) and (Ie).

The composition, for example as a part of a composite comprising fillers and/or fibres can also be used in other medical application such as orthopaedics as bone cement, in skull surgery or in orthopaedic applications.

EXPERIMENTAL PART

The following abbreviations are used in the Examples:
DBTDL: dibutyltin dilaurate, Sigma-Aldrich Co. (St Louis, MO, USA)
FTIR: Fourier-transform infrared
BisGMA: 2,2-bis(4-(2-hydroxy-3-methacryloxy)phenyl) propane, Esstech Inc. (Essington, PA, USA)
TEGDMA: triethylene glycol dimethacrylate, Sigma-Aldrich Co. (St Louis, MO, USA)
CQ: camphorquinone, Sigma-Aldrich Co. (St Louis, MO, USA)
DMAEMA: 2-(dimethylamino) ethyl methacrylate, Sigma-Aldrich Co. (St Louis, MO, USA)
Silaned $BaAlSiO_2$ filler particles, diameter 0.7 mm, manufactured by Schott, Landshut, Germany Example 1 Synthesis of Compound (Ic)

A mixture of 3-isopropenyl-α,α-dimethylbenzyl isocyanate (20.13 g. 0.1 mol), N-methyldiethanolamine (5.96 g. 0.05 mol), 50 mL extra dry tetrahydrofuran and two droplets of DBTDL was stirred at 40° C. The reaction was continued until the infrared absorbance peak of the —NCO group (2270 cm-1) disappeared in the FTIR spectra of the samples that were taken from the reaction medium. After removing the tetrahydrofuran by distillation under vacuum, the crude product was washed with n-hexane to remove the DBTDL. Then the colourless viscous liquid was dried under vacuum at 45° C. to obtain the compound (Ic) with a yield of 95%.

Example 2 Synthesis of Compound $(Id)^2$ (where x=2)

A mixture of 3-isopropenyl-α,α-dimethylbenzyl isocyanate (20.13 g. 0.1 mol), triethylene glycol (7.51 g. 0.05 mol), 50 mL extra dry tetrahydrofuran and two droplets of DBTDL was stirred at 45° C. The reaction was continued until the infrared absorbance peak of the —NCO group (2270 cm-1) disappeared in the FTIR spectra of the of the samples that were taken from the reaction medium. After removing the tetrahydrofuran by distillation under vacuum, the crude product was washed with n-hexane to remove DBTDL. Then the colourless viscous liquid was dried under vacuum at 45° C. to obtain compound $(Id)^2$ (where x=2) with a yield of 93%.

Example 3 Synthesis of Compound $(Id)^5$ (where x=5)

A mixture of 3-isopropenyl-α,α-dimethylbenzyl isocyanate (20.13 g. 0.1 mol), hexaethylene glycol (14.11 g. 0.05 mol), 50 mL extra dry tetrahydrofuran and two droplets of DBTDL was stirred at 50° C. The reaction was continued until the infrared absorbance peak of the —NCO group (2270 cm-1) disappeared in the FTIR spectra of the samples that were taken from the reaction medium. After removing the tetrahydrofuran by distillation under vacuum, the crude product was washed with n-hexane to remove DBTDL. Then the colourless viscous liquid was dried under vacuum at 45° C. to obtain compound $(Id)^5$ (where x=5) with a yield of 97%.

Example 4

Four different resin matrices of dental composites containing compound (Ic) as prepared in Example 1 were prepared according to the formulations shown in Table 1. A control sample did not contain the compound (Ic). All compounds were weighed and mixed under magnetic stirring for 3 hours. Thereafter, each resin matrix was mixed with silaned $BaAlSiO_2$ filler particles (diameter 0.7 mm, as explained above) in a high-speed mixing machine (SpeedMixer, DAC150 FVZ-K; Hauschild, Hamm, Germany) with a speed of 1900 rpm.

The mass ratio between resins matrix and fillers was 2:5 (wt/wt).

TABLE 1

| Resin matrix | Components (wt-%) | | | | |
|---|---|---|---|---|---|
| | BisGMA | TEGDMA | (Ic) | CQ | DMAEMA |
| Control | 49.3 | 49.3 | 0 | 0.7 | 0.7 |
| EC-1 | 44.3 | 44.3 | 10 | 0.7 | 0.7 |
| EC-2 | 39.3 | 39.3 | 20 | 0.7 | 0.7 |
| EC-3 | 34.3 | 34.3 | 30 | 0.7 | 0.7 |
| EC-4 | 29.3 | 29.3 | 40 | 0.7 | 0.7 |

The various composites were tested as described below.

Double Bond Conversion

Double bond conversion (DC %) during and after the photoinitiation of polymerization was monitored by Fourier transform infrared spectroscopy (FTIR) (Spectrum One, Perkin-Elmer, Beaconsfield Bucks, UK) with an attenuated total reflectance (ATR) accessory. The composites were analysed in a mould that was 1.5 mm thick and 4.5 mm in diameter. First, the spectrum of the unpolymerised sample was placed in the mould and measured. Then the sample was irradiated through an upper glass slide for 40 s with a visible light-curing unit (Elipar TM S10, 3M ESPE, Germany) producing an average irradiance of 1800 mW/cm$^2$ (Marc Resin Calibrator, BlueLight Analytics Inc., Canada). The sample was scanned for its FTIR spectrum after being irradiated for 40 s and 5 min after the beginning of irradiation. The DC was calculated from the aliphatic C=C peak at 1636 cm$^{-1}$ and normalized against phenyl ring peak at 1608 cm$^{-1}$ according to the formula $$DC = \frac{(A_{c=c}/A_{ph})_0 - (A_{c=c}/A_{ph})_t}{(A_{c=c}/A_{ph})_0} \times 100\%$$

where $A_{C=C}$ and $A_{ph}$ were the absorbance peak area of methacrylate C=C at 1636 cm$^{-1}$ and phenyl ring at 1608 cm$^{-1}$, respectively; $(A_{C=C}/A_{ph})_0$ and $(A_{C=C}/A_{ph})_t$ represented the normalised absorbency of the functional group at the radiation time of 0 and t, respectively; DC is the conversion of methacrylate C=C as a function of irradiation time. For each composite, five trials were performed and the average calculated Flexural Strength and Modulus Three-point bending test specimens (2×2×25 mm$^3$) were made from each tested composite. Bar-shaped specimens were made in half-split stainless-steel moulds between transparent Mylar sheets. Polymerisation of the materials was done using a hand light-curing unit (Elipar S10, 3M ESPE, St. Paul, MN, USA) for 20 s in five separate overlapping portions from both sides of the metal mould. The wavelength of the light was between 430 and 480 nm and light intensity was 1600 mW/cm$^2$. The specimens from each material (n=8) were stored in dry atmosphere at 37° C. for one day before testing. The three-point bending test was conducted according to the ISO 4049:2009 (test span: 20 mm, crosshead speed: 1 mm/min, indenter: 2 mm diameter). All specimens were loaded into a material testing machine (model LRX, Lloyd Instrument Ltd., Fareham, England) and the load-deflection curves were recorded with PC-computer software (Nexygen 4.0, Lloyd Instruments Ltd., Fareham, England).

Flexural strength ($\sigma f$) and flexural modulus (Ef) were calculated from the following formula (ISO 4049:2009)

$\sigma f = 3F_m L/(2bh^2)$ $Ef = SL^3/(4bh^3)$

Where $F_m$ is the applied load (N) at the highest point of a load-deflection curve, L is the span length (20 mm), b is the width of test specimens and h is the thickness of test specimens. S is the stiffness (N/m). S=F/d and d is the deflection corresponding to load F at a point in the straight-line portion of the trace.

Fracture Toughness

Single-edge-notched-beam specimens (2.5×5×25 mm$^3$) according to adapted ISO 20795-2 standard method (ASTM 2005) were prepared to determine the fracture toughness. A custom-made stainless-steel split mould was used, which enabled the specimen's removal without force. An accurately designed slot was fabricated centrally in the mould extending until its mid-height, which enabled the central location of the notch and optimisation of the crack length (x) to be half of the specimens' height. The restorative material was inserted into the mould placed over a Mylar-strip-covered glass slide in one increment. Before polymerisation a sharp and centrally located crack was produced by inserting a straight edged steel blade into the prefabricated slot. Polymerisation of the composite was carried out for 20 s in five separate overlapping portions. The upper side of the mould was covered with Mylar strip and glass slide from both sides of the blade, before being exposed to the polymerisation light. Upon the removal from the mould, each specimen was polymerised also on the opposite side. The specimens from each group (n=8) were stored dry at 37° C. for 24 h before testing. The specimens were tested in three-point bending mode, in a universal material testing machine at a crosshead speed of 1.0 mm/min.

The fracture toughness was calculated using the equation $K_{max} = [PL/BW^{3/2}]f(x)$ where f(x)=3/2×½ [1.99−x (1−x) (2.15−3.93x+2.7×2)]/2(1+2x) (1−x)3/2 and 0<x<1 with x=a/W. Here P is the maximum load in kilonewtons (kN), L is the span length (20 cm), B is the specimen thickness in centimetres (cm), W is the specimen width (depth) in cm, x is a geometrical function dependent on a/W and a is the crack length in cm.

Volumetric Shrinkage

The specimens' densities (n=3) were measured to determine volume shrinkage according to Archimedes' principle with a commercial density determination kit of the analytical balance (XS105, Mettler Toledo, Greifensee, Switzerland). The mass of the specimen was weighed in air and water, and density was calculated according to the equation $$D = \frac{M_1 \times D_w}{M_1 - M_2}$$

where D is the density of the sample, $M_1$ is the mass of the sample in air, $M_2$ is the mass of the sample in water, and $D_w$ is the density of water at the measured temperature. For each composite, six trials were performed respectively to calculate the densities of polymerised and unpolymerised samples. The volume shrinkage (VS) was expressed in % and calculated from the densities according to the equation $$VS = \frac{D_c - D_u}{D_c} \times 100\%$$

where $D_u$ is the density of the unpolymerised sample and $D_c$ is the density of the polymerised sample.

Shrinkage Stress

Glass fibre reinforced composite (FRC) rods with 4 mm diameter and 4 cm length had one of their flat surfaces ground with 180 grit silicon carbide sand paper. Two FRC rods were attached tightly to a universal testing machine (model LRX, Lloyd Instruments Ltd., Fareham, England) and the material to be tested was applied between the FRC rod surfaces. The height of the specimen was set at 2 mm. Two light units (Elipar S10, 3M ESPE, St. Paul, MN, USA) were used simultaneously for 20 s with the tips in close contact with the material specimen from both sides. Contraction forces were monitored for 5 min at room temperature (22° C.). Shrinkage stress was calculated by dividing the shrinkage force by the cross-section area of the FRC rod. The maximum shrinkage stress value was taken from the plateau at the end of shrinkage stress/time curve. Five specimens were tested for each experimental material.

The test results of the dental composites according to Table 1 for double bond conversion (Table 2), flexural strength (Table 3), flexural modulus (Table 4), fracture toughness (Table 5), volumetric shrinkage (Table 6) and shrinkage stress (Table 6 and FIG. 1) are shown below. In the tables, SD stands for standard deviation.

TABLE 2

|         | 40 s | SD  | 5 min | SD  |
|---------|------|-----|-------|-----|
| control | 63.3 | 0.6 | 65.8  | 0.4 |
| EC-1    | 63.6 | 1.4 | 66.2  | 1.1 |
| EC-2    | 61.3 | 0.4 | 64.7  | 0.3 |
| EC-3    | 60.3 | 0.6 | 64.2  | 0.8 |
| EC-4    | 59.7 | 1.6 | 63.4  | 2.1 |

The double bond conversion was measured after being irradiated for 40 s and 5 min. The results show that a significant amount of the double bonds was converted already after 40 seconds (at least 60%) and the conversion did not significantly increase with 5 minutes irradiation.

TABLE 3

|         | Mean  | SD   |
|---------|-------|------|
| Control | 114.2 | 9.7  |
| EC-1    | 120.4 | 11.6 |
| EC-2    | 112.8 | 10.2 |
| EC-3    | 104.8 | 10.8 |
| EC-4    | 94.0  | 7.2  |

Table 3 shows the flexural strength (MPa) of the various compositions. It can be seen that for some compositions according to the present disclosure, the results were better than for the control sample, while for others they were similar or slightly lower.

TABLE 4

|         | Mean | SD  |
|---------|------|-----|
| Control | 7487 | 695 |
| EC-1    | 7661 | 508 |
| EC-2    | 7286 | 391 |
| EC-3    | 6669 | 882 |
| EC-4    | 6096 | 528 |

Table 4 shows the flexural modulus (MPa) of the various compositions. It can be seen that the results are in line with the flexural strength results shown in Table 3.

TABLE 5

|         | Mean | SD   |
|---------|------|------|
| Control | 1.42 | 0.13 |
| EC-1    | 1.34 | 0.10 |
| EC-2    | 1.27 | 0.10 |
| EC-3    | 1.40 | 0.14 |
| EC-4    | 1.51 | 0.15 |

Table 5 shows the fracture toughness ($MPa \cdot m^{1/2}$) of each sample. Again. almost all samples had a fracture toughness similar or better than the control sample.

TABLE 6

|         | Mean | SD  |
|---------|------|-----|
| Control | 3.9  | 0.9 |
| EC-1    | 3.5  | 0.6 |
| EC-2    | 2.6  | 0.7 |
| EC-3    | 2.6  | 0.9 |
| EC-4    | 1.4  | 0.6 |

Table 6 gives the volumetric shrinkage (%) of the composite. All composites according to the present description had a lower volumetric shrinkage than the control sample.

TABLE 7

|         | Mean | SD   |
|---------|------|------|
| Control | 4.62 | 0.41 |
| EC-1    | 3.63 | 0.92 |
| EC-2    | 3.08 | 0.25 |
| EC-3    | 2.08 | 0.19 |
| EC-4    | 1.05 | 0.18 |

Table 7 shows the shrinkage stress of composites (MPa), which is also lower for each composite according to the present description. when compared to the control sample.

The shrinkage stress curves are shown in FIG. 1, wherein time in minutes is given in the abscissa and the stress in MPa in the ordinate. When looking from the upper part of the Figure, the results of the different samples are in the following order: the uppermost curve is for sample EC-4, then EC-3, EC-1, EC-2 and the lowest curve is for the control sample.

Example 5

Resin matrices of dental composites containing compound $(Id)^2$ (where x=2) were prepared according to the formulations shown in Table 8. All compounds were weighed and mixed under magnetic stirring. Experimental dental composites were prepared by mixing each resin matrix with silaned $BaAlSiO_2$ filler particles (diameter 0.7 mm) in a high-speed mixing machine as above in Example 4. The mass ratio between resins matrix and fillers was 2:5 (wt/wt). The materials were tested as above in Example 4, with the exception of double bond conversion, which test method is given below.

TABLE 8

| Resin matrix | Components (wt-%) | | | | |
|---|---|---|---|---|---|
|  | BisGMA | TEGDMA | (Id)2 | CQ | DMAEMA |
| Control | 49.3 | 49.3 | 0 | 0.7 | 0.7 |
| EC-5 | 44.3 | 44.3 | 10 | 0.7 | 0.7 |

TABLE 8-continued

| Resin matrix | Components (wt-%) | | | | |
|---|---|---|---|---|---|
| | BisGMA | TEGDMA | (Id)2 | CQ | DMAEMA |
| EC-6 | 39.3 | 39.3 | 20 | 0.7 | 0.7 |
| EC-7 | 34.3 | 34.3 | 30 | 0.7 | 0.7 |
| EC-8 | 29.3 | 29.3 | 40 | 0.7 | 0.7 |

Double Bond Conversion

Double bond conversion (DC %) during and after the photoinitiation of polymerisation was monitored by Fourier transform infrared spectroscopy (FTIR) (Spectrum One, Perkin-Elmer, Beaconsfield Bucks, UK) with an attenuated total reflectance (ATR) accessory. Composites were analysed in a mould that was 1.5 mm thick and 4.5 mm in diameter. First, the spectrum of the unpolymerised sample was placed in the mould and measured. Then the sample was irradiated through an upper glass slide for 60 s with a visible light-curing unit (Elipar TM S10, 3M ESPE, Germany) producing an average irradiance of 1800 mW/cm² (Marc Resin Calibrator, BlueLight Analytics Inc., Canada). The sample was scanned for its FTIR spectrum every 10 s until 60 s after the beginning of irradiation. The DC was calculated from the aliphatic C=C peak at 1636 cm$^{-1}$ and normalised against phenyl ring peak at 1608 cm$^{-1}$ according to the formula $$DC = \frac{(A_{c=c}/A_{ph})_0 - (A_{c=c}/A_{ph})_t}{(A_{c=c}/A_{ph})_0} \times 100\%$$

where $A_{C=C}$ and $A_{ph}$ were the absorbance peak area of methacrylate C=C at 1636 cm$^{-1}$ and phenyl ring at 1608 cm$^{-1}$, respectively; $(A_{C=C}/A_{ph})_0$ and $(A_{C=C}/A_{ph})_t$ represented the normalized absorbency of the functional group at the radiation time of 0 and t, respectively; DC is the conversion of methacrylate C=C as a function of radiation time. For each composite, five trials were performed.

The results of the tests double bond conversion (Table 9), flexural strength and modulus (Table 10) and shrinkage stress (Table 11 and FIG. 2) of the dental composites prepared according to Table 8 are shown below. In the tables, SD stands for standard deviation and Contr for the control sample.

TABLE 9

| | Contr. | | EC-5 | | EC-6 | | EC-7 | | EC-8 | |
|---|---|---|---|---|---|---|---|---|---|---|
| Time | Mean | SD | Mean | SD | Mean | SD | Mean | SD | Mean | SD |
| 0 | 0 | 0 | 0 | 0 | 0 | 0 | 0 | 0 | 0 | 0 |
| 10 | 47.5 | 0.8 | 33.9 | 1.9 | 27.7 | 1.0 | 21.9 | 2.4 | 23.6 | 1.5 |
| 20 | 56.9 | 0.2 | 52.1 | 0.8 | 47.3 | 1.7 | 44.1 | 0.5 | 43.2 | 1.4 |
| 30 | 59.5 | 0.4 | 56.6 | 0.8 | 53.6 | 1.4 | 52.4 | 0.8 | 52.2 | 1.4 |
| 40 | 60.9 | 0.3 | 58.5 | 0.6 | 57.1 | 0.4 | 54.9 | 2.6 | 55.5 | 1.9 |
| 50 | 62.2 | 0.9 | 59.5 | 0.9 | 58.0 | 0.8 | 57.6 | 1.0 | 57.3 | 1.3 |
| 60 | 62.2 | 0.5 | 60.7 | 1.0 | 58.4 | 1.0 | 58.5 | 1.0 | 59.2 | 2.6 |

Table 9 gives the double bond conversion in percentage, with respect to the irradiation time (in seconds). The control sample was the fastest in conversion, but the end results at 60 seconds are very similar for each composite.

TABLE 10

| | Flexural strength | | Flexural modulus | |
|---|---|---|---|---|
| | Mean | SD | Mean | SD |
| control | 102.3 | 16.9 | 6556.1 | 351.9 |
| EC-5 | 126.9 | 8.1 | 7680.4 | 444.5 |
| EC-6 | 106.8 | 13.0 | 7242.7 | 391.2 |
| EC-7 | 98.8 | 8.4 | 5509.0 | 498.0 |
| EC-8 | 80.2 | 5.7 | 4983.5 | 399.4 |

Table 10 shows the flexural strength (MPa) and flexural modulus (MPa) of the various compositions. It can be seen that for some compositions according to the present disclosure, the results were better than for the control sample, while for others they were similar or slightly lower.

TABLE 11

| | Mean | SD |
|---|---|---|
| Control | 5.0 | 0.3 |
| EC-5 | 4.2 | 0.3 |
| EC-6 | 3.6 | 0.5 |
| EC-7 | 2.3 | 0.4 |
| EC- | 1.6 | 0.2 |

Table 11 shows the shrinkage stress of composites (MPa), which is also lower for each composite according to the present description, when compared to the control sample.

Figure 2:
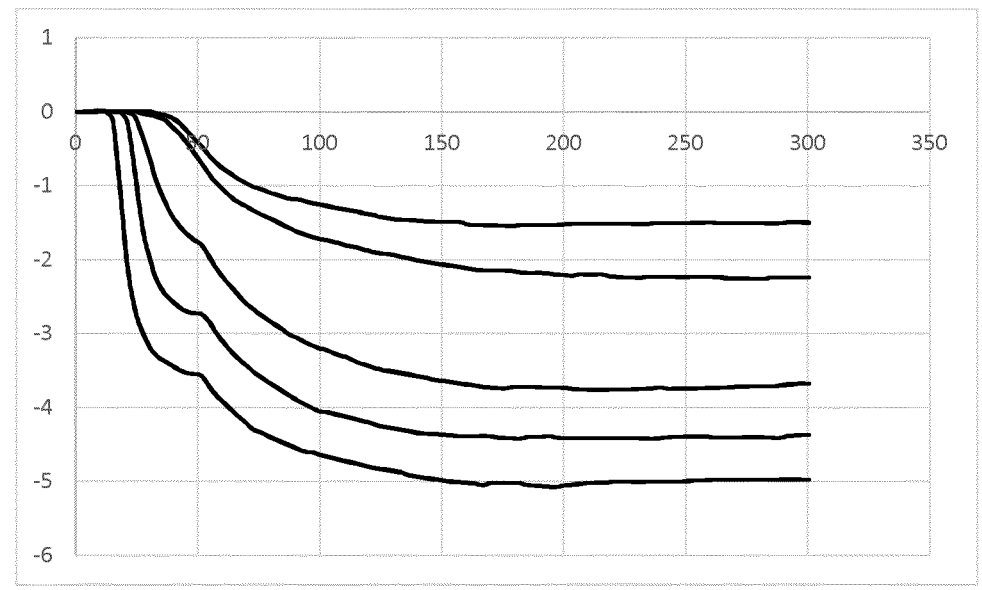
FIG. 2 illustrates the shrinkage stress curves of samples prepared according to Example 5.

The shrinkage stress curves are shown in FIG. 2, wherein time in minutes is given in the abscissa and the shrinkage stress in MPa in the ordinate. When looking from the upper part of the Figure, the results of the different samples are in the following order: the uppermost curve is for sample EC-8, then EC-7, EC-6, EC-5 and the lowest curve is for the control sample.

Example 6

Resin matrices of dental composites containing 40 wt-% of compound (Id)$^2$ (where x=2), compound (Id)$^5$ (where x=5) or compound (Ic), were prepared by adding 40 wt-% of the corresponding monomer into BisGMA/TEGDMA (50/50 wt/wt) resin matrix. 0.7 wt-% of CQ and 0.7 wt-% of DMAEMA were added as photoinitiator system. All compounds were weighed and mixed under magnetic stirring. Experimental dental composites were prepared by mixing each resin matrix with silaned BaAlSiO$_2$ filler particles (diameter 0.7 mm) in a high-speed mixing machine (as above in Example 4). The mass ratio between resins matrix and fillers was 2:5 (wt/wt). The materials were tested as above in Example 4, with the exception of double bond conversion, which test method is given below.

TABLE 12

| Resin matrix | Components (wt-%) | | | | |
|---|---|---|---|---|---|
| | BisGMA | TEGDMA | (Id)$^2$/ (Id)$^5$/(Ic) | CQ | DMAEMA |
| Control | 49.3 | 49.3 | 0 | 0.7 | 0.7 |
| EC-9 | 29.3 | 29.3 | 40 | 0.7 | 0.7 |
| EC-10 | 29.3 | 29.3 | 40 | 0.7 | 0.7 |
| EC-11 | 29.3 | 29.3 | 40 | 0.7 | 0.7 |

Double Bond Conversion

Double bond conversion (DC %) during and after the photoinitiation of polymerisation was monitored by Fourier transform infrared spectroscopy (FTIR) (Spectrum One, Perkin-Elmer, Beaconsfield Bucks, UK) with an attenuated total reflectance (ATR) accessory. Composites were analysed in a mould that was 1.5 mm thick and 4.5 mm in diameter. First, the spectrum of the unpolymerised sample was placed in the mould and measured. Then the sample was irradiated through an upper glass slide for 60 s (40 s for EC-11) with a visible light-curing unit (Elipar TM S10, 3M ESPE, Germany) producing an average irradiance of 1800 mW/cm² (Marc Resin Calibrator, BlueLight Analytics Inc., Canada). The sample was scanned for its FTIR spectrum every 10 s until 60 s (40 s for EC-11) after the beginning of irradiation. The DC was calculated from the aliphatic C=C peak at 1636 cm$^{-1}$ and normalised against phenyl ring peak at 1608 cm$^{-1}$ according to the formula $$DC = \frac{(A_{c=c}/A_{ph})_0 - (A_{c=c}/A_{ph})_t}{(A_{c=c}/A_{ph})_0} \times 100\%$$

where $A_{C=C}$ and $A_{ph}$ were the absorbance peak area of methacrylate C=C at 1636 cm$^{-1}$ and phenyl ring at 1608 cm$^{-1}$, respectively; $(A_{C=C}/A_{ph})_0$ and $(A_{C=C}/A_{ph})_t$ represented the normalized absorbency of the functional group at the radiation time of 0 and t, respectively; DC is the conversion of methacrylate C=C as a function of radiation time. For each composite, five trials were performed.

The results of double bond conversion (Table 13), flexural strength and modulus (Table 14) and shrinkage stress (Table 15 and FIG. 3) of the dental composites prepared according to Table 12 are shown below. In the tables. SD stands for standard deviation.

TABLE 13

| Time | Control | | EC-9 | | EC-10 | | EC-11 | |
|---|---|---|---|---|---|---|---|---|
| | Mean | SD | Mean | SD | Mean | SD | Mean | SD |
| 0 | 0.0 | 0.0 | 0.0 | 0.0 | 0.0 | 0.0 | 0.0 | 0.0 |
| 10 | 47.5 | 0.8 | 23.6 | 1.5 | 20.2 | 0.3 | 29.6 | 2.5 |
| 20 | 56.9 | 0.2 | 43.2 | 1.4 | 41.3 | 0.7 | 51.0 | 2.9 |
| 30 | 59.5 | 0.4 | 52.2 | 1.4 | 54.3 | 0.7 | 57.1 | 1.5 |
| 40 | 60.9 | 0.3 | 55.5 | 1.9 | 59.2 | 0.9 | 59.6 | 1.6 |
| 50 | 62.2 | 0.9 | 57.3 | 1.3 | 61.4 | 0.5 | | |
| 60 | 62.2 | 0.5 | 59.2 | 2.6 | 62.6 | 0.4 | | |

Table 13 gives the double bond conversion in percentage, with respect to the irradiation time (in seconds). The control sample was the fastest in conversion, but the end results at 60 seconds are very similar for each composite.

TABLE 14

| | Flexural strength | | Flexural modulus | |
|---|---|---|---|---|
| | Mean | SD | Mean | SD |
| control | 10..3 | 16.9 | 6556.1 | 351.9 |
| EC-9 | 80.2 | 5.7 | 4983.5 | 399.4 |
| EC-10 | 91.0 | 6.1 | 4751.7 | 587.4 |
| EC-11 | 94.0 | 7.2 | 6069.2 | 528.0 |

Table 14 shows the flexural strength (MPa) and flexural modulus (MPa) of the various compositions. It can be seen that for some compositions according to the present disclosure, the results were better than for the control sample, while for others they were similar or slightly lower.

TABLE 15

| | Mean | SD |
|---|---|---|
| Control | 5.0 | 0.3 |
| EC-9 | 1.6 | 0.2 |
| EC-10 | 2.4 | 0.4 |
| EC-11 | 1.1 | 0.2 |

Table 15 shows the shrinkage stress of composites (MPa), which is significantly lower for each composite according to the present description, when compared to the control sample.

Figure 3:
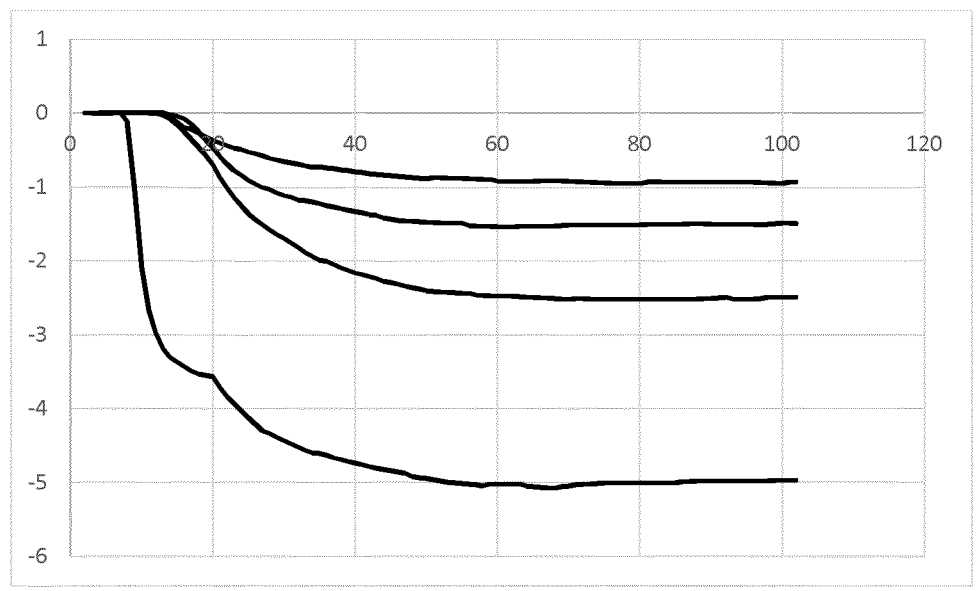
FIG. 3 illustrates the shrinkage stress curves of samples prepared according to Example 6.

The shrinkage stress curves are shown in FIG. 3, wherein time in minutes is given in the abscissa and the shrinkage stress in MPa in the ordinate. When looking from the upper part of the Figure, the results of the different samples are in the following order: the uppermost curve is for sample EC-11, then EC-9, EC-10, and the lowest curve is for the control sample.

The invention claimed is:

1. A dental composition comprising 10-50 wt-% of a methacrylate-based first matrix component, a polymerisation system and as a second matrix component 1-50 wt-% of a compound having a general formula (I)

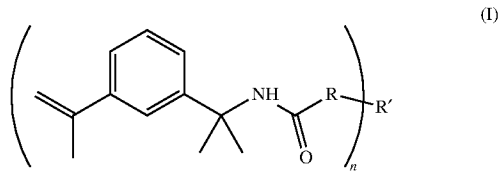

(I)

wherein when n=1, R=NH, R' is (Ia) or (Ib)

(Ia)

wherein k is 2 or 3,

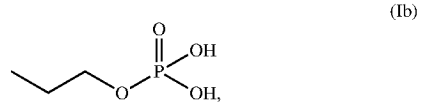

(Ib)

when n=2, R=O, R' is (Ic) or (Id)

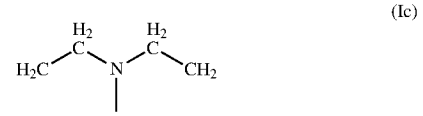

(Ic)

-continued

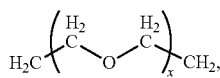
(Id)

wherein x=1-12,
when n=2, R=NH or O, R' is (Ie)

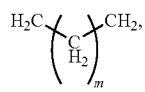
(Ie)

wherein m=0-16, and
when n=2, R=O, R' is (If)

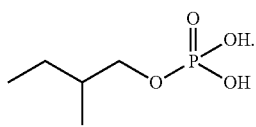
(If)

2. The dental composition according to claim 1, wherein the amount of the first matrix component is 30-50 wt-%.

3. The dental composition according to claim 1, wherein the amount of the second matrix component is 3-35 wt-%.

4. The dental composition according to claim 1, further comprising 10-45 wt-% of a methacrylate-based third matrix component different from the first matrix component.

5. The dental composition according to claim 1, wherein the first matrix component and an optional third matrix component are independently selected from a group consisting of methyl methacrylate, ethyl methacrylate, n-butyl methacrylate, isobutyl methacrylate, 2-ethylhexyl methacrylate, 2-hydroxyethyl methacrylate, cyclohexyl methacrylate, isobornyl methacrylate, tetrahydrofurfuryl methacrylate, benzyl methacrylate, methacryloyloxydecyl dihydrogen phosphate, morpholinoethyl methacrylate, acrylic acid, diethylene glycol dimethacrylate, triethylene glycol dimethacrylate, diurethane dimethacrylate and 2,2-bis(4-(2-hydroxy-3-methacryloxy) phenyl)-propane, and mixtures thereof.

6. The dental composition according to claim 1, further comprising a filler material.

7. The dental composition according to claim 6, wherein the filler material is selected from the group consisting of glass ionomer fillers, colour pigments, inert ceramics, hydroxyl apatite, Al2O3, ZrO2l, silver, zerogels, bioactive glasses, radio-opaque materials, and mixtures thereof.

8. The dental composition according to claim 1, further comprising a fibre reinforcing material.

9. The dental composition according to claim 8, wherein the fibre reinforcing material is selected from the group consisting of inert glass fibres, bioactive glass fibres, sol-gel processed silica fibres, aluminium oxide-based fibres, zirconia fibres, apatite fibres, quartz fibres and mixtures thereof or polymer based fibres.

10. A method of treating a patient in need of dental care, the method comprising administering to the dental patient an amount of the dental composition according to claim 1.

11. The method of claim 10, wherein the dental composition is administered as a dental restoration material, a dental adhesive, a dental cement, a post and core material, an endo-crown material, or for a pontic in fixed partial dentures.

* * * * *